United States Patent
Declerck et al.

(10) Patent No.: US 8,078,258 B2
(45) Date of Patent: Dec. 13, 2011

(54) ASSESSMENT OF VASCULAR COMPARTMENT VOLUME FOR PET MODELLING

(75) Inventors: Jerome Declerck, Oxford (GB); Kevin Scott Hakl, Oxford (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 667 days.

(21) Appl. No.: 12/121,279

(22) Filed: May 15, 2008

(65) Prior Publication Data

US 2008/0319304 A1 Dec. 25, 2008

(30) Foreign Application Priority Data

May 18, 2007 (GB) .................................. 0709561.5
Dec. 3, 2007 (GB) .................................. 0723521.1

(51) Int. Cl.
*A61B 5/05* (2006.01)
(52) U.S. Cl. ................... 600/420; 600/407; 250/363.03; 250/363.04
(58) Field of Classification Search .......... 600/407–420; 250/363.03, 363.04
See application file for complete search history.

(56) References Cited

U.S. PATENT DOCUMENTS

| | | | |
|---|---|---|---|
| 7,069,068 B1 * | 6/2006 | Ostergaard | 600/420 |
| 2004/0236085 A1 * | 11/2004 | Luthra et al. | 536/1.11 |
| 2005/0113667 A1 | 5/2005 | Schlyer et al. | |
| 2006/0284096 A1 * | 12/2006 | Krieg et al. | 250/363.03 |
| 2007/0299335 A1 | 12/2007 | Declerck et al. | |
| 2009/0238767 A1 * | 9/2009 | Hummel et al. | 424/9.32 |

FOREIGN PATENT DOCUMENTS

WO  WO 2006/119085 A2  11/2006

OTHER PUBLICATIONS

Soret, M. et al., "Partial-Volume Effect in PET Tumor Imaging", Journal of Nuclear Medicine, vol. 48, No. 6, p. 932-945, Jun. 2007.
Srikanchana, R. et al., "A Comparison of Pharmacokinetic Models of Dynamic Contrast Enhanced MRI", Computer-Based Medical Systems, p. 361-366, Jun. 2004.
Rousset, O. G., et al., "Correction for Partial Volume Effects in PET: Principle and Validation", The Journal of Nuclear Medicine, vol. 39, No. 5, p. 904-911, May 1998.
Great Britain Search Report dated Apr. 1, 2008 (Five (5) pages).

* cited by examiner

*Primary Examiner* — Sanjay Cattungal
(74) *Attorney, Agent, or Firm* — Crowell & Moring LLP

(57) ABSTRACT

A method is described for acquiring and analysing the data produced by Positron Emission Tomography (PET), which method provides for an accurate estimation of vascular compartment volume, $V_B$. An MRI scan and the PET scan is performed simultaneously and the results of the former is used to derive a value for $V_B$. The value so derived is then used in pharmacokinetic modelling along with the results of the functional scan.

5 Claims, 1 Drawing Sheet

ASSESSMENT OF VASCULAR COMPARTMENT VOLUME FOR PET MODELLING

The invention is concerned with the estimation of vascular compartment volume for pharmo-kinetic modelling of Positron Emission Tomography (PET) data.

BACKGROUND AND SUMMARY OF THE INVENTION

Positron Emission Tomography (PET) is a nuclear medical imaging technique which provides a three-dimensional map of functional processes in the human or animal body.

A radioactive (positron emitting) tracer isotope is incorporated in a metabolically active molecule such as 18-F fluoro-2-deoxy-2-glucose (FDG, a sugar analogue) which is ingested in a subject. Other radiolabelled molecules which may be used in PET include 3'-deoxy-3'-[18-F]-fluorothymidine (FLT) and 6-[(18)F]fluoro-L-DOPA (FDOPA). These molecules can be imaged by a scanner or camera which detects and records the gamma type radiation resulting from a collision between an emitted positron and an electron in the surrounding matter.

The radiation so produced is released as two photons travelling in near opposite directions. Hence, by detecting corresponding photons within a small co-incidence timing window (an event), a line of response (LOR) along which the origin of the radiation lies can be deduced. Deduction (or analysis) of many such lines allows a three-dimensional map of the tracer distribution to be produced that maps onto the spatial dimensions of the subject. The number of individual events emitted and hence, detected, is related to the rate of radioactive decay and hence, the concentration of radioactive tracer in the subject. Confidence in the deduced radioactivity distribution from the lines of response is proportional to the number of events detected which is related in turn to the time interval over which the events are recorded. Some tracers, such as FDG, are known to accumulate in organs or tissues that have high rates of glucose metabolism, for example tumor cells and muscles. In such cases, events are recorded for an interval of time after the tracer has had time to accumulate and an average rate of decay is estimated for that interval. Such images are known as static scans.

Alternatively, several such images can be produced over a certain period of time while the tracer distribution is still evolving, to form a sequence of temporal frames analogous to a video recording of the functional activity as labelled by the radiotracer. These sequences are conventionally called dynamic images and can be 2 or 3 dimensional.

Analysis of how the radiotracer distributes over time as well as space provides additional important information about the functional behaviour of the subject over and above that attainable by static images.

The study of dynamic function of tracers in the body requires analysis and modelling of the cellular processes in which the tracer is involved: pharmaco-kinetic modelling (PKM). PKM models the molecular pathways as a series of diffusion and active transport processes, (also reversible and irreversible binding processes) starting from the blood vessels in capillaries, which diffuse the tracer into the interstitial tissue, cells, etc., all of which represented as a set of boxes with defined concentration change rates. As an example, FDG floating in the blood is taken up in the cell and then metabolised as FDG-6-phosphate. FDG-6-P is then not metabolised further and is either trapped in the cell or washes out (in the liver, for instance). FIG. 1 illustrates the modelling.

The pharmacokinetic approach is fundamental to modelling drug action on tissues of interest. It is routinely utilized in drug development techniques as the medical imaging modalities allow the visualization of some in vivo cellular processes.

When measuring tracer activity with PET, the total activity $C_M$ within each voxel is measured. Thus, it includes contributions from the tracer concentration in blood vessel $C_B$ and in the cell tissue $C_T$ (as FDG and FDG-6 respectively when the injected tracer is FDG).

As the tracer uptake occurs over time, a series of samples of the concentration in the voxel over time using a dynamic image should enable the identification of each concentration and rate constants.

Estimation of $V_B$ from the dynamic PET image with PKM is possible, but may not be very accurate, particularly since the useful time frames of the dynamic images for estimation of $V_B$ are the earlier ones, when the tracer is still predominantly in the blood and starts to be rapidly taken up in the cell. However, because it is a rapid process, the early time frames of PET cover a short time interval and are therefore very noisy, making the estimation of $V_B$ relatively unreliable.

As an alternative to using only the dynamic PET information, $V_B$ can be pre-estimated from atlases and known average anatomy information. However, this method does not take into account variation which may arise from the patient physiology and anatomy as well as pathophysiology of the disease (for example, in cancerous tumours, angiogenesis involves the local creation of a massive amount of blood vessels, which increases $V_B$ significantly). The technique is used routinely in studies, but the estimation of $V_B$ lacks robustness, which impacts the estimation of the rate constants, which is what the clinician is really after.

Magnetic Resonance Imaging (MRI) can produce equivalent image quality in terms of noise in a much shorter time interval than PET. The resolution in MRI images is also much finer, which enables the fast acquisition of fairly well contrasted dynamic sequences of images. Unfortunately, there are a number of limitations which prevent the use of contrast enhanced MRI to model cellular processes as finely as PET can, mainly because a) the contrast agents need to be injected in much higher concentrations and b) the agents are usually much larger molecules which do not penetrate easily into the cell. Rather, the agents usually travel in the blood stream or leak into the interstitial tissue. This makes MRI a modality of choice to estimate blood vessel concentration volumes.

The estimation of the ratio of blood vessel volume is well established in the literature: Tofts and Kermode (in "Measurement of the blood-brain barrier permeability and leakage space using dynamic MR imaging", Magn Reson Med. 1991 February; 17(2):357-67) show a method of modelling the pharmaco-kinetic of the Gd-DTPA agent in the blood, where they model $v_1$, which is the fraction of volume occupied by the space in which the agent leaks into. This parameter $v_1$ is specific to Gd-DTPA as a blood pool agent as this capillary structure is slightly altered in presence of certain types of tumour, making them more permeable and allowing the DTPA molecule to leak out of the capillary space. However, assuming that we used another agent which was not leaking into the intra-cellular space but, rather, was staying in the blood vessels even in presence of tumours (a bigger molecule would do), the method of Tofts and Kermode would be exactly be applicable and the calculated $v_1$ would be exactly the same as the $V_B$ we are estimating in PET pharmaco-kinetic modelling.

The integration of PET and MRI equipment in a single system is known, see for example US Patent 2005/0113667 or WO 2006/119085. Such systems allow for accurate localization of metabolic activity in an anatomic framework.

According to the invention, a method of generating and processing a set of Positron Emission Tomography (PET) scan images administering a PET scan contrast agent and a magnetic resonance imaging (MRI) contrast agent to a subject; simultaneously performing a PET scan and an MRI scan on the subject to generate PET scan images and corresponding data from the MRI scan; calculating $V_B$, the fraction of pixel volume occupied by blood vessels, using data acquired from the MRI scan; and performing pharmacokinetic analysis based on i) the value of $V_B$ so derived and ii) the PET scan images. Moreover, apparatus for acquiring and processing a set of Positron Emission Tomography (PET) scan images comprises a PET scanner; an MRI scanner, said PET scanner and said MRI scanner being configured to perform simultaneous scans of a subject; and a processor; wherein the process is configured, to receive data from each of the PET scanner and the MRI scanner; to calculate $V_B$, the fraction of pixel volume occupied by blood vessels, using the data acquired during the MRI scan; and to perform pharmacokinetic analysis based on i) the value of $V_B$ so derived, and ii) the PET scan images.

Other objects, advantages and novel features of the present invention will become apparent from the following detailed description of the invention when considered in conjunction with the accompanying drawings.

DETAILED DESCRIPTION OF THE INVENTION

Figure 1:
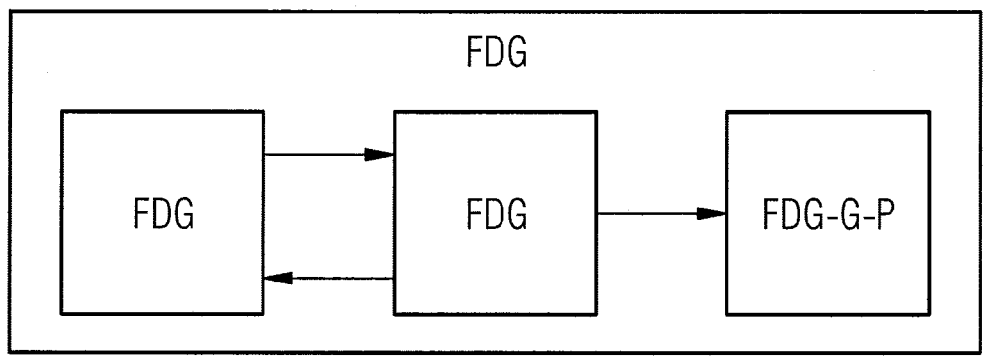
FIG. 1 illustrates the mathematical model used to describe the dynamic function of tracers in the body.
Figure 2:
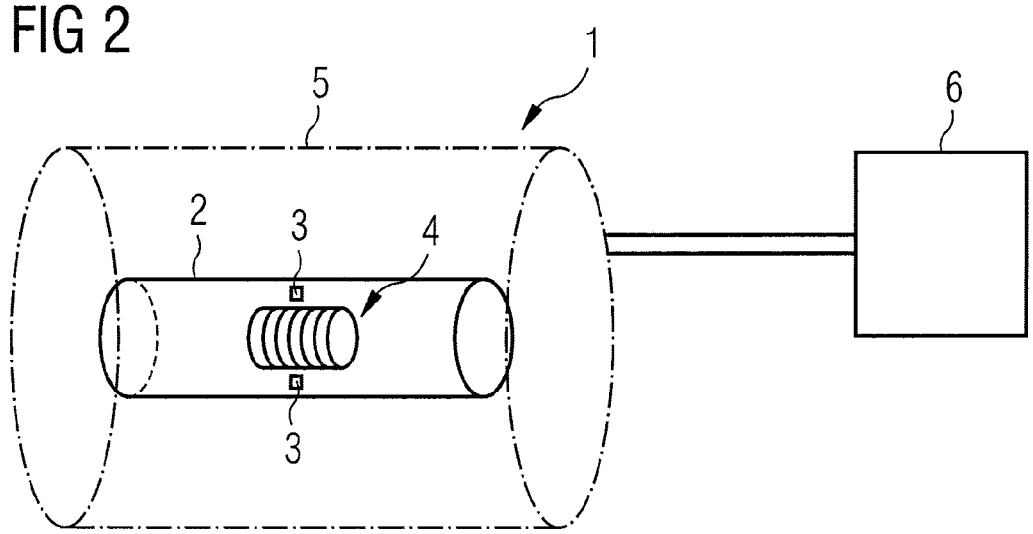
FIG. 2 illustrates an example of apparatus of the invention.

Referring to FIG. 2, apparatus of the invention, generally designated 1, includes a PET scanner 2 having a ring of scintillators 3 and a series of RF coils 4 located in the main magnet 5 of an MRI scanner (other components not shown).

Such a combination of PET and MRI scanning apparatus enables simultaneous and iso-volumic acquisition of a volume of interest in PET and MRI. With such a device, a combination of a radioactive PET compound and a blood stream MRI contrast agent is injected simultaneously, and both PET and MR dynamic images are acquired.

The PET/MRI apparatus are controlled by processor 6. Software applications allow user interaction to set parameters for a particular protocol and initiate scanning. Data acquisition and storage would also typically be controlled by processor 6.

The dynamic MRI is acquired over the early part of the imaging protocol as the blood stream information quickly reaches some equilibrium, and it is possible to estimate $V_B$ from these early rapid frames. In addition a dynamic PET image is acquired as in conventional dynamic PET acquisition protocol.

The value $V_B$ estimated from the MRI image to recover rate constants from the PET image. As MR produces far less noisy images than PET, the estimation of $V_B$ will be more reliable. Moreover the reduction of the number of parameters to estimate in the dynamic PET will make the estimation of the rate constants more reliable.

The estimation of $V_B$ and subsequent estimation of rate constants can be achieved by execution of further applications by processor 6.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A method of processing a set of Positron Emission Tomography (PET) scan images comprising the steps of:
    administering a PET scan contrast agent and a magnetic resonance imaging (MRI) contrast agent to a subject;
    simultaneously performing a PET scan and an MRI scan on the subject to generate PET scan images and corresponding data from the MRI scan;
    calculating $V_B$, the fraction of pixel volume occupied by blood vessels, using data acquired from the MRI scan; and
    performing pharmacokinetic analysis based on i) the value of $V_B$ so derived and ii) the PET scan images.

2. A method according to claim 1, wherein the PET scan contrast agent is 18-F fluoro-2-deoxy-2-glucose (FDG).

3. A method according to claim 1 wherein the PET scan contrast agent is 3'-deoxy-3'-[18-F]-fluorothymidine (FLT).

4. A method according to claim 1 wherein the PET scan contrast agent is 6-[(18)F]fluoro-L-DOPA (FDOPA).

5. Apparatus comprising:
    a PET scanner;
    an MRI scanner, said PET scanner and said MRI scanner being configured to perform simultaneous scans of a subject; and
    a processor;
    wherein the process is configured,
        to receive data from each of the PET scanner and the MRI scanner;
        to calculate $V_B$, the fraction of pixel volume occupied by blood vessels, using the data acquired during the MRI scan; and
        to perform pharmacokinetic analysis based on i) the value of $V_B$ so derived, and ii) the PET scan images.

* * * * *